US012635939B2

(12) United States Patent
An

(10) Patent No.: US 12,635,939 B2
(45) Date of Patent: May 26, 2026

(54) PAIN MEASURING DEVICE AND PAIN MEASURING METHOD

(71) Applicant: DAEGU GYEONGBUK INSTITUTE OF SCIENCE AND TECHNOLOGY, Daegu (KR)

(72) Inventor: Jinung An, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 527 days.

(21) Appl. No.: 18/073,831

(22) Filed: Dec. 2, 2022

(65) Prior Publication Data

US 2023/0172533 A1　　Jun. 8, 2023

(30) Foreign Application Priority Data

Dec. 6, 2021　(KR) ......................... 10-2021-0172787

(51) Int. Cl.
*A61B 5/00* (2006.01)
*G06N 3/02* (2006.01)
(52) U.S. Cl.
CPC ............. *A61B 5/4827* (2013.01); *G06N 3/02* (2013.01)
(58) Field of Classification Search
CPC .................................................. A61B 5/4827
See application file for complete search history.

(56) References Cited

U.S. PATENT DOCUMENTS

2009/0270757 A1* 10/2009 Backonja ............. A61B 5/4824
600/555
2016/0279382 A1* 9/2016 Gordon ................ A61B 5/4824

2019/0043322 A1* 2/2019 Tachi ...................... G06F 3/016
2019/0134396 A1* 5/2019 Toth .......................... A43B 3/34
2021/0128921 A1* 5/2021 Srivastava ........... A61B 5/0077
2022/0207425 A1* 6/2022 Nakae ..................... A61B 5/372
2023/0277122 A1* 9/2023 Rezai ...................... A61B 5/165

FOREIGN PATENT DOCUMENTS

| | | |
|---|---|---|
| JP | 2018191773 | 12/2018 |
| JP | 2019093095 | 6/2019 |
| JP | 2020203121 | 12/2020 |
| JP | 2021168752 | 10/2021 |
| KR | 10-2014-0065168 | 5/2014 |

OTHER PUBLICATIONS

Ahmed Bilal Ashraf et al., "The Painful Face—Pain Expression Recognition Using Active Appearance Models", IImage and Vision Computing, vol. 27, Issue 12, Nov. 1, 2009, pp. 1788-1796.

* cited by examiner

*Primary Examiner* — Daniel L Cerioni

(74) *Attorney, Agent, or Firm* — LEX IP MEISTER, PLLC

(57) ABSTRACT

Provided are a pain measuring device and a main measuring method. More particularly, the pain measuring device may control a temperature provided from a temperature stimulator, receive, from a user input portion, a user input for recording a level of stimulation according to the temperature, obtain, from a camera, image data representing a change in an external shape of a user according to the stimulation, obtain, from a sensor, biodata representing a biological change of the user according to the stimulation, and obtain information about a level of pain experienced by the user according to the stimulation based on data corresponding to the user input, the image data, and the biodata.

4 Claims, 8 Drawing Sheets

| | |
|---|---|
| | |
| | |
| | 32℃ |
| | |
| | |
| | |

Figure 7:
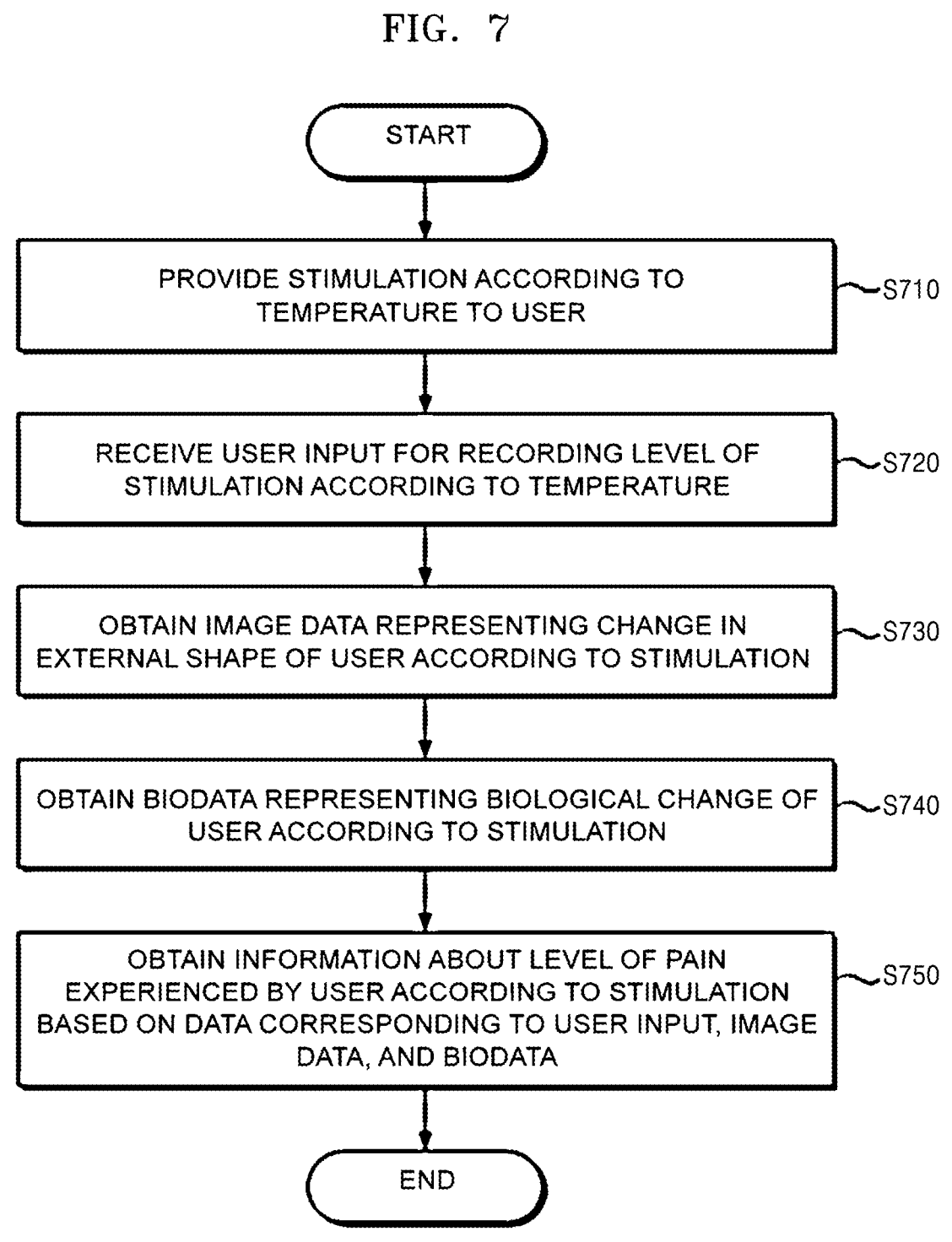

START

PROVIDE STIMULATION ACCORDING TO TEMPERATURE TO USER ⎯ S710

RECEIVE USER INPUT FOR RECORDING LEVEL OF STIMULATION ACCORDING TO TEMPERATURE ⎯ S720

OBTAIN IMAGE DATA REPRESENTING CHANGE IN EXTERNAL SHAPE OF USER ACCORDING TO STIMULATION ⎯ S730

OBTAIN BIODATA REPRESENTING BIOLOGICAL CHANGE OF USER ACCORDING TO STIMULATION ⎯ S740

OBTAIN INFORMATION ABOUT LEVEL OF PAIN EXPERIENCED BY USER ACCORDING TO STIMULATION BASED ON DATA CORRESPONDING TO USER INPUT, IMAGE DATA, AND BIODATA ⎯ S750

END

FIG. 8

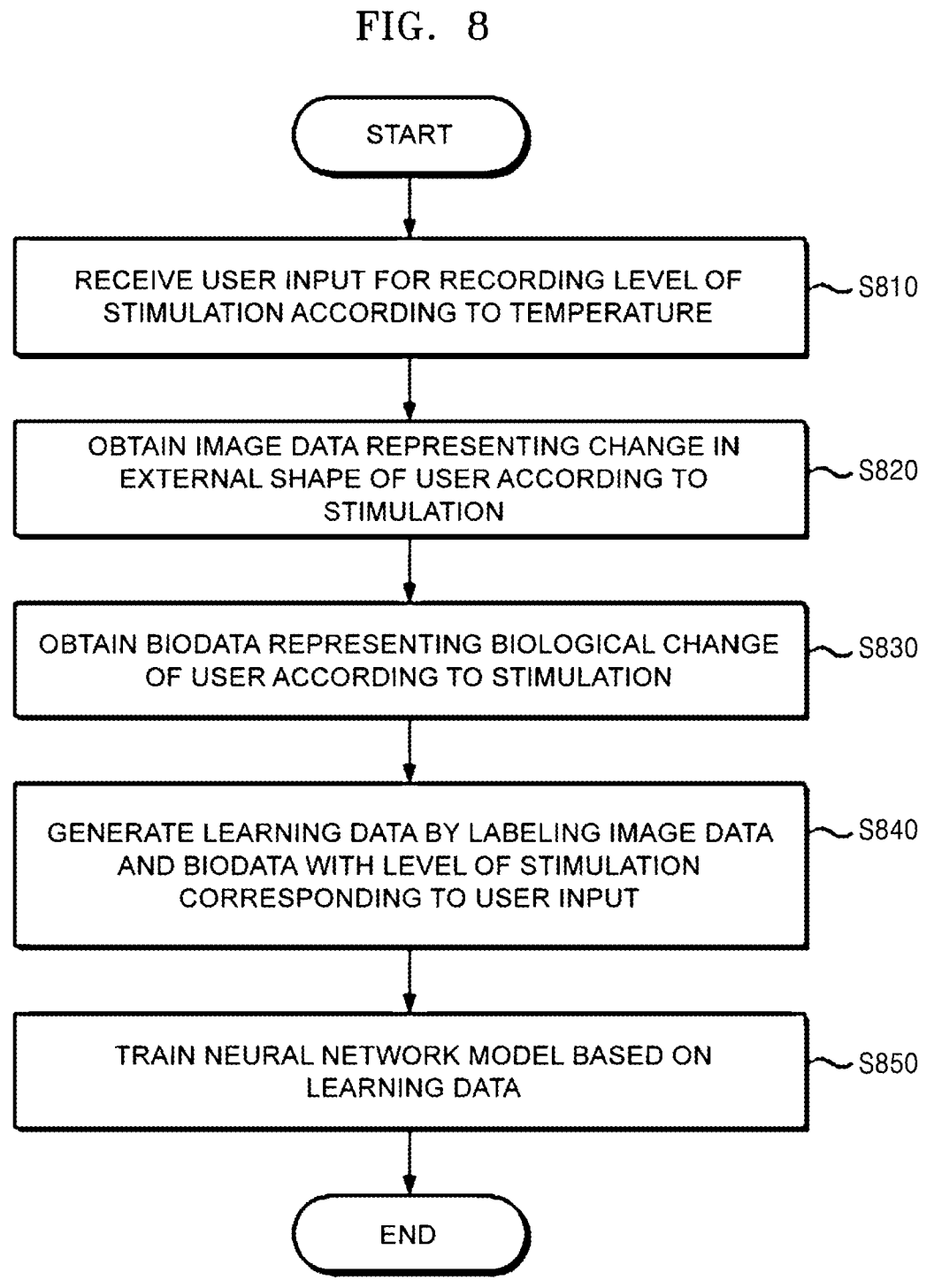

START

RECEIVE USER INPUT FOR RECORDING LEVEL OF STIMULATION ACCORDING TO TEMPERATURE ⟶ S810

OBTAIN IMAGE DATA REPRESENTING CHANGE IN EXTERNAL SHAPE OF USER ACCORDING TO STIMULATION ⟶ S820

OBTAIN BIODATA REPRESENTING BIOLOGICAL CHANGE OF USER ACCORDING TO STIMULATION ⟶ S830

GENERATE LEARNING DATA BY LABELING IMAGE DATA AND BIODATA WITH LEVEL OF STIMULATION CORRESPONDING TO USER INPUT ⟶ S840

TRAIN NEURAL NETWORK MODEL BASED ON LEARNING DATA ⟶ S850

END

PAIN MEASURING DEVICE AND PAIN MEASURING METHOD

CROSS-REFERENCE TO RELATED APPLICATION

This application is based on and claims priority under 35 U.S.C. § 119 to Korean Patent Application No. 10-2021-0172787, filed on Dec. 6, 2021, in the Korean Intellectual Property Office, the disclosure of which is incorporated by reference herein in its entirety.

BACKGROUND

1. Field

The present disclosure relates to pain measuring devices and pain measuring methods, and more particularly, to pain measuring devices configured to measure a level of pain caused by stimulation according to temperature and methods of controlling the pain measuring devices.

2. Description of the Related Art

In accordance with the recent advances in the field of health-care, there has been a growing demand for new technologies which enable precise measurement of level of pain experienced by a user according to temperature and correct diagnosis or proper treatment based thereon.

According to the existing technologies, a simple ratio between a current perception threshold (CPT) at which a user (subject) responds to current stimulation and a pain equivalent current (PEC) at which a user feels pain may be calculated as a level of pain, and by using the correlation between the level of pain and a visually analogue scale (VAS) or a facial expression scale, a value of pain may be calculated.

However, in the related arts, as the VAS or the facial expression scale represents numerical sensation of pain according to subjective judgment by a subject, and thus does not technically include subjective and quantitative values of pain, defining these scales as the ground truth and matching an intensity of current stimulation to values of the VAS/facial expression scale based thereon to simply convert the pain into numerical values is considered merely as another representation by the existing VAS or facial expression scale.

That is, the existing technologies are merely an improvement over conventional electrostimulation pain threshold measuring devices, etc. and have limitation in quantitatively and subjectively quantify the level of pain according to stimulation.

SUMMARY

Provided are pain measuring devices capable of quantitatively and objectively measuring a level of pain experienced by a user, and pain measuring methods.

Additional aspects will be set forth in part in the description which follows and, in part, will be apparent from the description, or may be learned by practice of the presented embodiments of the disclosure.

According to an aspect of an embodiment, a pain measuring device includes a temperature stimulator, a user input portion, a camera, a sensor, a memory in which at least one instruction is stored, and a processor configured to execute the at least one instruction, wherein, by executing the at least one instruction, the processor may control a temperature provided from the temperature stimulator, receive, from the user input portion, a user input for recording a level of stimulation according to the temperature, obtain, from the camera, image data representing a change in an external shape of a user according to the stimulation, obtain, from the sensor, biodata representing a biological change of the user according to the stimulation, and obtain information about a level of pain experienced by the user according to the stimulation based on data corresponding to the user input, the image data, and the biodata.

The temperature stimulator may include a plurality of Peltier elements, and the processor may control the temperature stimulator to provide different temperatures through each of elements in a first group and elements in a second group, among the plurality of Peltier elements.

The elements in the first group may be elements corresponding to a preset figure, among the plurality of Peltier elements, and the elements in the second group may be the rest of the plurality of Peltier elements, which are different from the elements corresponding to the preset figure.

The processor may obtain the information about a level of pain experienced by the user according to the stimulation by inputting the data corresponding to the user input, the image data, and the biodata to a trained neural network model.

The processor may generate learning data by labeling the image data and the biodata with a level of the stimulation corresponding to the user input, and train the neural network model based on the learning data.

The image data may include at least one of information about a facial expression of the user, information about eyes of the user, and information about a gesture of the user.

The biodata may include at least one of data about a pulse wave of the user, data about an oxygen saturation of the user, and data about an electrocardiogram of the user.

According to an aspect of another embodiment, a pain measuring method includes controlling a temperature provided from a temperature stimulator, receiving a user input for recording a level of stimulation according to the temperature, obtaining image data representing a change in an external shape of a user according to the stimulation, obtaining biodata representing a biological change of the user according to the stimulation, and obtaining information about a level of pain experienced by the user according to the stimulation based on data corresponding to the user input, the image data, and the biodata.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 3 to 5 are diagrams illustrating in detail configuration of a temperature stimulator according to some embodiments;

FIG. 7 is a flowchart illustrating a pain measuring method according to an embodiment; and FIG. 8 is a flowchart illustrating a method of training a neural network model according to an embodiment.

DETAILED DESCRIPTION

Figure 1:
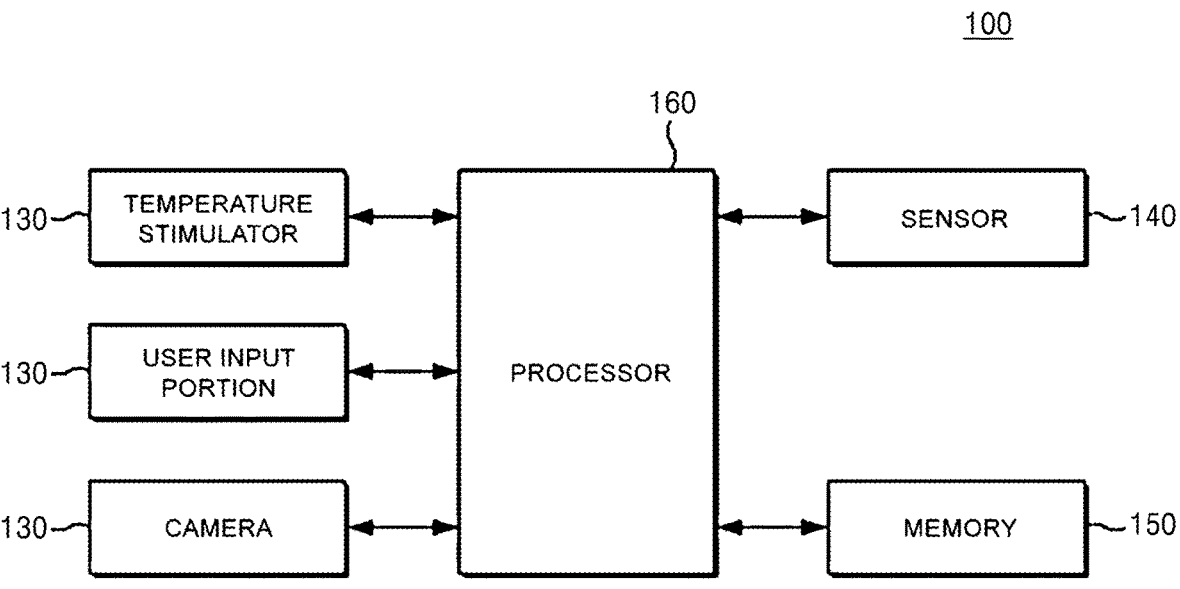
FIG. 1 is a diagram briefly illustrating components of a pain measuring device according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

As the present disclosure allows for various changes and numerous embodiments, exemplary embodiments will be illustrated in the drawings and described in detail in the written description. However, this is not intended to limit embodiments to particular modes of practice, and it is to be appreciated that all modifications, equivalents, and/or alternatives are encompassed in embodiments. As for the description of the drawings, like reference numerals may denote like elements.

In the description of embodiments, certain detailed explanations of the related art are omitted when it is deemed that they may unnecessarily obscure the essence of the present disclosure.

In addition, embodiments may be embodied in many different forms and the technical ideas of the present disclosure should not be construed as being limited to the embodiments set forth herein; rather, these embodiments are provided so that this disclosure will be thorough and complete, and will fully convey the concept of embodiments to those skilled in the art.

The terms used in the present specification are merely used to describe exemplary embodiments, and are not intended to limit the scope of right. An expression used in the singular encompasses the expression of the plural, unless it has a clearly different meaning in the context.

In the present disclosure, it is to be understood that the terms such as "have," "may have," "include," and "may include" are intended to indicate the existence of the features, numbers, actions, parts, components, etc. disclosed in the specification, and are not intended to preclude the possibility that other features may exist.

As used herein, the expressions "A or B," "at least one of A and/or B," "one or more of A and/or B," etc. include any and all combinations of one or more of the associated listed items. For example, when "A or B," "at least one of A and B," or "at least one of A or B" is included, (1) at least one A may be included, (2) at least one B may be included, or (3) at least one A and at least one B may be included.

While such terms as "first," "second," etc., may be used to describe various components regardless of order and/or importance, such components must not be limited to the above terms. The above terms are used only to distinguish one component from another.

When a component (e.g., a first component) is "operatively or communicatively coupled with/to" or "connected to" another component (e.g., a second component), it shall be understood that the first component is coupled/connected to the second component directly or via another component (e.g., a third component).

On the other hand, when a component (e.g., a first component) is "directly coupled with/to" or "directly connected to" another component (e.g., a second component), it shall be understood that no other component (e.g., a third component) exists between the first component and the second component.

The expression of "configured to" used herein may be replaced with, for example, "suitable for," "having the capacity to," "designed to," "adapted to," "made to," or "capable of" as applicable. Hardware-wise, the expression "configured to" may not necessarily mean "specifically designed to."

Instead, in some cases, the expression "a device configured to . . . " may mean that "a device is capable of . . . together with other devices and parts. For example, the expression "a processor configured to perform A, B, and C" may mean a dedicated processor for performing A, B, and C (e.g., an embedded processor) or a generic-purpose processor (e.g., a central processing unit or an application processor) capable of performing A, B, and C by executing one or more software programs stored in a memory device.

In embodiments, a "module" or a "portion" may perform at least one function or operation and may be implemented by a hardware, a software, or a combination thereof. Moreover, a plurality of "modules" or a plurality of "portions" may be integrated into at least one module and implemented as at least one processor, except for a "module" or a "portion" which needs to be implemented as a specific hardware.

Furthermore, various elements and areas in the drawings are schematically drawn. Thus, the technical ideas of the present disclosure are not limited by relative sizes or distances illustrated in the accompanying drawings.

Hereinafter, embodiments of the present disclosure will be described in detail with reference to the accompanying drawings so that a person with ordinary skill in the art may easily perform the present disclosure.

Figure 2:
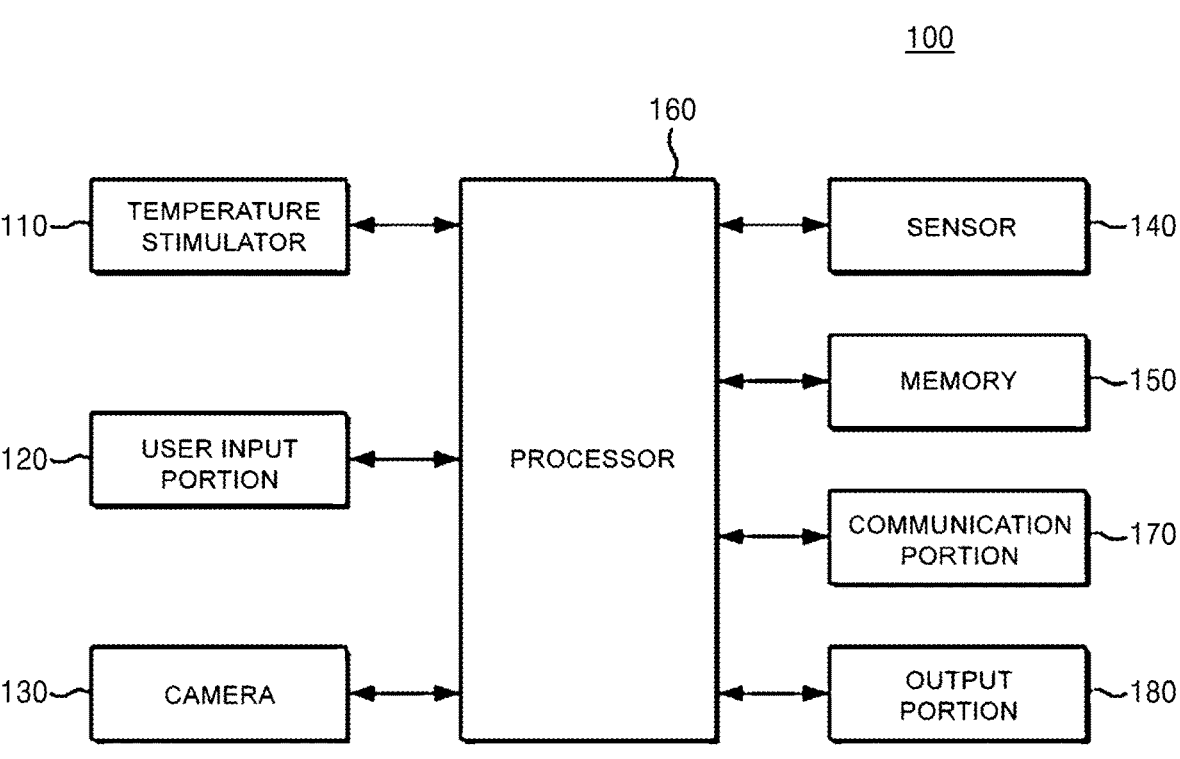
FIG. 2 is a diagram illustrating in detail components of a pain measuring device according to an embodiment.

FIG. 1 is a diagram briefly illustrating components of a pain measuring device 100 according to an embodiment. FIG. 2 is a diagram illustrating in detail components of the pain measuring device 100 according to an embodiment.

The pain measuring device 100 according to the present disclosure may refer to a device capable of measuring a level of pain caused by stimulation according to temperature. More specifically, the pain measuring device 100 may provide various types of stimulation according to a thermal sensation or a cold sensation to a user (a subject), and measure a level of pain experienced by the user according to the stimulation. Hereinafter, various embodiments of the present disclosure are described on the premise that the pain measuring device 100 includes the components shown in FIG. 1 or FIG. 2. However, the following embodiments may also be implemented through communication between the pain measuring device 100 and an external device in which some components of the pain measuring device 100 according to the present disclosure are included.

As illustrated in FIG. 1, the pain measuring device 100 according to an embodiment of the present disclosure may include a temperature stimulator 110, a user input portion 120, a camera 130, at least one sensor 140, a memory 150, and a processor 160. In addition, as illustrated in FIG. 2, the pain measuring device 100 according to the present disclosure may further include a communication portion 170 and an output portion 180. However, the components shown in FIGS. 1 and 2 are just examples, and other new components may be added to the components shown in FIGS. 1 and 2 or some of the component shown in FIGS. 1 and 2 may be omitted when carrying out the present disclosure.

The temperature stimulator 110 may provide stimulation according to temperature to a user. More specifically, the temperature stimulator 110 may include a plurality of Peltier elements. The Peltier element may refer to an electronic element capable of providing a cold sensation or a thermal sensation by using the Peltier effects which is a phenomenon in which, when a current flows to a thermocouple, a heat generation or heat absorption reaction occurs at each contact of the thermocouple, in addition to the generation of Joule's heat by the current. Specific configuration of the temperature stimulator 110 is described with reference to FIGS. 3 to 5.

The user input portion 120 may receive a user input for recording a level of stimulation according to temperature. More specifically, the user input portion 120 may receive a user input for self-recording a level of stimulation sensed by a user during when the stimulation according to temperature is provided through the temperature stimulator 110. For example, the user input portion 120 may include at least one of a keyboard, a mouse, a microphone, and a remote control signal receiver. Moreover, the user input portion 120 may be implemented as a touch screen integrated with a display to be described below.

The camera 130 may obtain image data about a user. The camera 130 may include an image sensor, and the image sensor may convert light coming through a lens into an electrical image signal. More specifically, there may be a single camera 130 or two or more cameras 130, and the camera 130 may obtain image data representing a change in an external shape of a user according to temperature stimulation. The sensor 140 may be included in the pain measuring device 100 as a component thereof or may be implemented as a separate device from the pain measuring device 100.

The sensor 140 may obtain biodata of a user. More specifically, there may be a single sensor 140 or two or more sensors 140, and the sensor 140 may obtain biodata representing a biological change of a user according to temperature stimulation. For example, the sensor 140 may be a biosensor 140 which is attached to the body of the user and obtains biodata of the user. The sensor 140 may be included in the pain measuring device 100 as a component thereof or may be implemented as a separate device from the pain measuring device 100.

At least one instruction regarding the pain measuring device 100 may be stored in the memory 150. In addition, an operating system (O/S) to drive the pain measuring device 100 may be stored in the memory 150. Various software programs or applications for operating the pain measuring device 100 according to embodiments of the present disclosure may also be stored in the memory 150. The memory 150 may include a semiconductor memory such as a flash memory, etc., or a magnetic storage medium such as a hard disk, etc.

More specifically, various software modules for operation of the pain measuring device 100 according to embodiments of the present disclosure may be stored in the memory 150, and the processor 160 may execute the various software modules stored in the memory 150 to control the operations of the pain measuring device 100. That is, the memory 150 may be accessed by the processor 160, and reading/recording/modification/deletion/update, etc. of data may be performed by the processor 160.

The term "memory 150" used herein may also include the memory 150, read-only memory (ROM, not shown) and random-access memory (RAM, not shown) in the processor 160, or a memory card (not shown) mounted onto the pain measuring device 100 (e.g., a micro SD card and a memory stick).

More specifically, in various embodiments of the present disclosure, various types of information, such as information about temperature corresponding to a target pain index, data corresponding to a user input, image data, biodata, information about a level of pain experienced by a user, information about a neural network model, etc. may be stored in the memory 150. In addition to the foregoing, other various necessary information may be stored in the memory 150 within a range to achieve the object of the present disclosure, and as the information stored in the memory 150 may be received from a server or an external device or input by a user, the information may be updated.

The processor 160 may control all operations of the pain measuring device 100. More specifically, the processor 160 may be connected with other components of the pain measuring device 100, i.e., the temperature stimulator 110, the user input portion 120, the camera 130, the at least one sensor 140, the memory 150, the communication portion 170, and the output portion 180, and control all operations of the pain measuring device 100.

The processor 160 may be implemented in various forms. For example, the processor 160 may be implemented as at least one of an application specific integrated circuit (ASIC), an embedded processor, a microprocessor, a hardware control logic, a hardware finite state machine (FSM), and a digital signal process (DSP).

The term "processor 160" used herein may include a central processing unit (CPU), a graphic processing unit (GPU), a main processing unit (MPU), etc.

More specifically, in various embodiments of the present disclosure, the processor 160 may perform a series of processes to obtain information about a level of pain experienced by a user. Hereinafter, various embodiments describing the control by the processor 160 are provided.

In an embodiment, the processor 160 may control the temperature provided from the temperature stimulator 110. More specifically, the processor 160 may control a current provided to each of the plurality of Peltier elements included in the temperature stimulator 110 to control a temperature provided from each of the plurality of Peltier elements such that a temperature corresponding to a target pain index is provided to a user. For example, the processor 160 may further include a module for universal asynchronous receiver/transmitter (UART) communications, a module for pulse width modulation (PWM) control, a module for voltage control, etc., and there is no limitation on specific hardware components of the processor 160.

The processor 160 may control the temperature stimulator 110 such that all of the plurality of Peltier elements provide the same temperature. In addition, the processor 160 may control the temperature stimulator 110 such that different temperatures are provided through each of elements in a first group and elements in a second group among the plurality of Peltier elements. The elements in the first group may be elements corresponding to a preset figure, among the plurality of Peltier elements, and the elements in the second group may be the rest of the plurality of Peltier elements, which are different from the elements corresponding to the preset figure. The embodiments in which different temperatures are provided by each of the plurality of Peltier elements are described in detail with reference to FIGS. 3 to 5.

The processor 160 may receive from the user input portion 120 a user input for recording a level of stimulation according to temperature. More specifically, the processor 160 may receive a user input for recording which level among preset levels of stimulation a level of stimulation sensed by a user corresponds to during when the stimulation according to temperature is provided from the temperature stimulator 110.

For example, the processor 160 may receive a user input through a keyboard or a mouse included in the user input portion 120, and when a user inputs a user input by using a remote control, the processor 160 may receive the user input through a remote control signal receiver included in the user input portion 120. The processor 160 may also receive a user input based on a user touch input through a touch screen. The user interface (UI) is described in detail in relation to the reception of user input with reference to FIG. 6.

The processor 160 may obtain from the camera 130 image data representing a change in an external shape of a user according to stimulation. For example, the image data may include at least one of information about a facial expression of the user, information about eyes of the user, and information about a gesture of the user. The obtaining of the image data may be continuously performed in real time during when the stimulation according to temperature is provided from the temperature stimulator 110, and accordingly, the processor 160 may obtain various information such as a change in a facial expression of a user, a change in eyes of the user, a change in a gesture of the user, etc. according to temperature change.

The processor 160 may obtain information about a facial expression of a user by inputting image data to a trained facial expression analysis model, may obtain information about eyes of a user by inputting image data to a trained eye analysis model, and may obtain information about a gesture of a user by inputting image data to a trained gesture analysis model.

The processor 160 may obtain from the sensor 140 biodata representing a biological change of a user according to stimulation. For example, the biodata may include at least one of data about a pulse wave of the user, data about an oxygen saturation of the user, and data about an electrocardiogram of the user. The obtaining of the biodata may also be performed continuously in real time during when the stimulation according to temperature is provided from the temperature stimulator 110.

The processor 160 may obtain biodata of a user by using a pulse wave sensor for sensing a pulse wave, an oxygen saturation sensor for measuring an oxygen level of blood of the user, an electrocardiogram sensor for measuring an electrocardiogram of the user, etc. The pulse wave sensor, the oxygen saturation sensor, or the electrocardiogram sensor may be attached to a part of the body of the user, such as a finger, to sense bio-information of the user.

The processor 160 may obtain information about a level of pain experienced by a user according to stimulation based on data corresponding to a user input, image data, and biodata. More specifically, the processor 160 may obtain information about a level of pain experienced by a user by using a predefined algorithm or a look-up table. In addition, the processor 160 may obtain information about a level of pain experienced by a user by using a trained neural network model.

In the present disclosure, the term "information about a level of pain" may collectively refer to information about various pain indexes, such as sensitivity to temperature difference, pain sensing temperature, pain endurance temperature, pain duration, pain attenuation phase, pain pattern, etc.

For example, when the neural network model is trained to obtain information about a level of pain experienced by a user in response to input of data corresponding to a user input, image data, and biodata, the processor 160 may input the data corresponding to a user input, the image data, and the biodata to the trained neural network model to obtain information about a level of pain experienced by a user.

The neural network model may receive as an input at least one of information about a facial expression of a user, information about eyes of a user, and information about a gesture of a user, which are obtained based on image data along with data corresponding to a user input or biodata and output information about a level of pain experienced by a user.

For example, when the neural network model is trained to obtain information about a level of pain experienced by a user in response to input of image data and biodata, the processor 160 may generate learning data by labeling the image data and the biodata with a level of stimulation corresponding to the user input and train the neural network model based on the learning data.

As described above, the obtaining of the image data and the biodata may be performed in real time during when the stimulation according to temperature is provided from the temperature stimulator 110. Accordingly, the processor 160 may correlate a level of stimulation corresponding to a user input with image data and biodata obtained at the same time point as when the user input is received to label the image data and the biodata with the level of stimulation corresponding to the user input. In this manner, learning data which may be used for supervised learning of the neural network model may be generated.

The communication portion 170 may include a circuit and may perform communication with an external device. More specifically, the processor 160 may receive various data or information from an external device connected through the communication portion 170, and may also transmit various data or information to an external device.

The communication portion 170 may include at least one of a WiFi module, a Bluetooth module, a wireless communication module, a near field communication (NFC) module, and an ultra wide band (UWB) module. More specifically, the WiFi module and the Bluetooth module may perform communication by using the WiFi method and the Bluetooth method, respectively. When the WiFi module or the Bluetooth module is used, various connection information such as a service set identifier (SSID), etc. may be received or transmitted first for communication connection, and then various information may be further received and transmitted.

Moreover, the wireless communication module may perform communications according to various communication standards such as IEEE, Zigbee, 3rd generation (3G), 3G partnership project (3GPP), long term evolution (LTE), 5th generation (5G), etc. The NFC module may perform communications based on the NFC method using the band of 13.56 MHz among a plurality of radio frequency identification (RFID) frequency bands, such as 135 kHz, 13.56 MHz, 433 MHz, 860 MHz to 960 MHz, 2.45 GHz, etc. The UWB module may precisely measure a time of arrival (ToA), which is a time taken for a pulse to arrive at a target object and an angle of arrival (AoA), which is an angle of arrival of a pulse in a transmitter through communication between UWB antennas, and thus, may precisely recognize a distance and a position indoors within the margin of error of several centimeters.

More specifically, in various embodiments of the present disclosure, the communication portion 170 may receive image data or biodata from an external device. The communication portion 170 may also transmit a control signal to an external device to obtain image data or biodata. In addition, the communication portion 170 may transmit information about a level of pain experienced by a user to an external device.

The output portion 180 may include a circuit, and the processor 160 may output through the output portion 180 various functions that may be performed by the pain measuring device 100. The output portion 180 may include at least one of a display, a speaker, and an indicator.

The display may output image data according to the control by the processor 160. More specifically, the display may output an image prestored in the memory 150 according to the control by the processor 160. The display may be implemented as a liquid crystal display (LCD) panel, organic light-emitting diodes (OLED), etc., and in some cases, the display may also be implemented as a flexible display, a transparent display, etc. However, the type of the display according to the present disclosure is not limited thereto. More specifically, the display according to an embodiment of the present disclosure may display a user interface (UI) stored in the memory 150. An example of the UI is described with reference to FIG. 6.

The speaker may output audio data according to the control by the processor 160 and the indicator may light up according to the control by the processor 160.

More specifically, in various embodiments of the present disclosure, the output portion 180 may output information for guiding a user to record a level of stimulation according to temperature. The output portion 180 may display information about a level of pain experienced by a user. The output portion 180 may output information corresponding to image data and biodata of the user. That is, various information including the aforementioned information may be output in a form of image through the display, may be output in a form of voice through the speaker, and may be provided to a user though the lighting-up of the indicator.

According to various embodiments of the present disclosure, as the pain measuring device 100 of the present disclosure uses not only subjective information such as recordal of level of pain experienced by a user but also objective information such as image data/biodata, the pain measuring device 100 may quantitatively and objectively measure a level of pain experienced by a user. Accordingly, by considering various indexes relevant to a level of pain experienced by a user in real time, a correct diagnosis and a proper treatment may be provided to a user.

Figure 4:
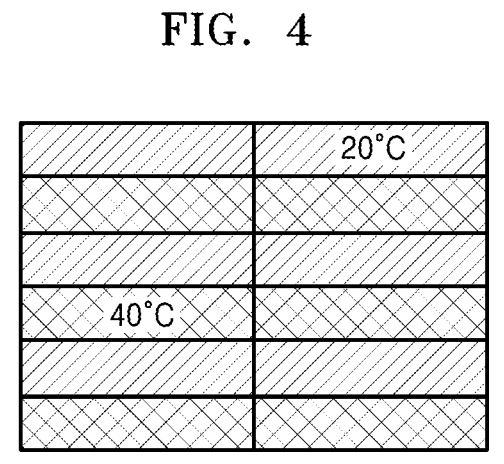
Figure 5:
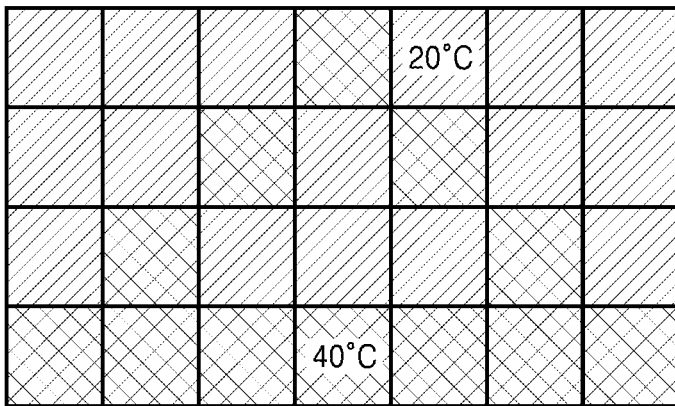

FIGS. 3 to 5 are diagrams illustrating in detail configuration of the temperature stimulator 110 according to some embodiments.

As described above, the temperature stimulator 110 according to the present disclosure may be configured to provide simulation according to temperature to a user and may include a plurality of Peltier elements for providing a cold sensation or a thermal sensation.

As illustrated in FIGS. 3 and 4, the plurality of Peltier elements according to the present disclosure may be 12 Peltier elements, and the 12 Peltier elements may be arranged in a matrix of 6×2.

When the plurality of Peltier elements are implemented as illustrated in FIGS. 3 and 4, the processor 160 may control the temperature stimulator 110 such that all of the plurality of Peltier elements provide the same temperature. For example, as illustrated in FIG. 3, all of the plurality of Peltier elements may provide the temperature of 32° C.

The processor 160 may control the temperature stimulator 110 such that different temperatures are provided through each of the elements in the first group and the elements in the second group among the plurality of Peltier elements. For example, as illustrated in FIG. 4, among the plurality of Peltier elements, the Peltier elements corresponding to a first row, a third row, and a fifth row may provide the temperature of 20° C., and the Peltier elements corresponding to a second row, a fourth row, and a sixth row may provide the temperature of 40° C.

When, among the plurality of Peltier elements, the elements in the first group and the elements in the second group provide different temperatures from each other, various pain indexes may be measured more safely, compared to the case where the same temperature is provided from the plurality of Peltier elements. More specifically, when, among the plurality of Peltier elements, the elements in the first group and the elements in the second group provide different temperatures from each other, as warm stimulation and cold stimulation are applied on the skin of a user at the same time, the user may sense pain due to the so-called thermal grill illusion phenomenon. Accordingly, instead of simply measuring a threshold temperature which is bearable to a user, information about various pain indexes according to an integrated mechanism of the nervous system may be obtained.

As illustrated in FIG. 5, the plurality of Peltier elements according to the present disclosure may be 28 Peltier elements, and the 289 Peltier elements may be arranged in a matrix of 4×7.

When the plurality of Peltier elements are implemented as illustrated in FIG. 5, the processor 160 may control the temperature stimulator 110 to provide the temperature of 40° C. through the Peltier elements corresponding to a first row and a fourth column, a second row and a third column, a second row and a fifth column, a third row and a second column, a third row and a sixth column, and the entire fourth row, and provide the temperature of 20° C. through the rest of the Peltier elements.

That is, the processor 160 may provide different temperatures through each of the elements in the first group and the elements in the second group, among the plurality of Peltier elements, wherein the elements in the first group may be elements corresponding to a preset figure, and the elements in the second group may be the rest of the Peltier elements, except for the elements corresponding to the preset figure. For example, the preset figure may be a triangle as illustrated in FIG. 5; however, the present disclosure is not limited thereto.

When the temperature of the elements corresponding to the preset figure is controlled to be different through the plurality of Peltier elements as illustrated in FIG. 5, a user having a normal temperature receptor may be able to normally recognize a pattern of the figure, whereas a user having a problem with a temperature receptor may have difficulty in recognizing the pattern of the figure normally. Accordingly, when the temperature of the elements corresponding to the preset figure is controlled to be different through the plurality of Peltier elements as illustrated in FIG. 5, by controlling the plurality of Peltier elements such that a figure optimized according to a type of measurement target pain index is shown, information about various pain indexes, such as sensitivity to temperature difference or pattern of pain may be obtained.

11 12

Figure 6:
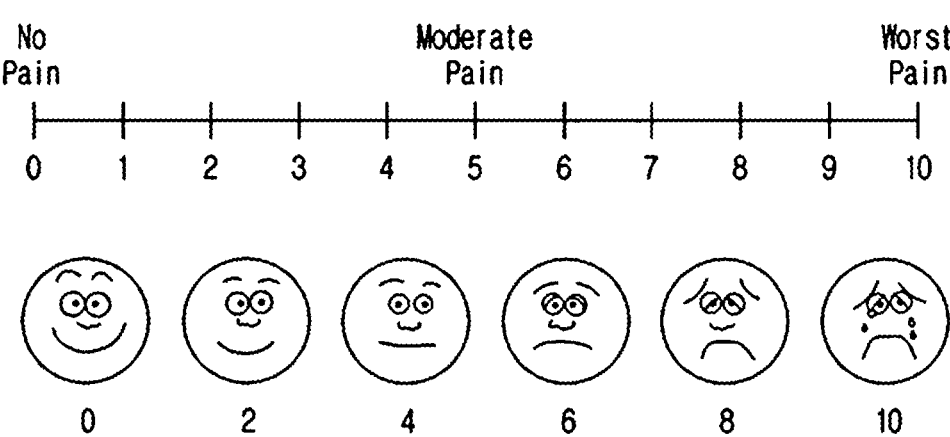
FIG. 6 is a diagram illustrating a user interface according to an embodiment.

FIG. 6 is a diagram illustrating a user interface according to an embodiment.

As described above, the processor 160 may receive from the user input portion 120 a user input for recording a level of stimulation according to temperature. More specifically, a user may self-record a level of stimulation according to temperature by referring to a visual analogue scale (VAS), a numerical rating scale, a pain questionnaire word test, etc. which represent levels of stimulation during when stimulation according to temperature is provided through the temperature stimulator 110.

For example, as illustrated in FIG. 6, the processor 160 may control a display such that a user interface for showing a VAS representing a level of stimulation is displayed. The user interface may include information showing a level of stimulation (level of pain) on a scale of 0 to 10 and emoticons respectively corresponding to levels of stimulation of 0, 2, 4, 6, 8, and 10.

When a user interface illustrated in FIG. 6 is displayed, a user may input a number from 0 to 10 by using a keyboard, or click on a number or an emoticon corresponding to a level of stimulation by using a mouse to record a level of stimulation sensed during when the stimulation according to temperature is provided. Furthermore, the user may utter a voice corresponding to a number or a letter corresponding to a level of stimulation to record the level of stimulation through a microphone.

The user interface illustrated in FIG. 6 is just an example, and the user interface may include various other information in addition to the information included in the user interface shown in FIG. 6.

FIG. 7 is a flowchart illustrating a pain measuring method according to an embodiment.

With reference to FIG. 7, the pain measuring device 100 according to an embodiment of the present disclosure may provide stimulation according to temperature (S710). The pain measuring device 100 may control the temperature stimulator 110 such that all of the plurality of Peltier elements provide the same temperature. In addition, the pain measuring device 100 may control the temperature stimulator 110 such that different temperatures are provided through each of elements in the first group and elements in the second group among the plurality of Peltier elements.

The pain measuring device 100 may receive a user input for recording a level of stimulation according to temperature (S720). The pain measuring device 100 may receive a user input for recording which level among preset levels of stimulation a level of stimulation sensed by a user corresponds to during when the stimulation according to temperature is provided from the temperature stimulator 110. For example, when a user interface showing a visual scale of levels of stimulation is displayed, the pain measuring device 100 may receive a user input for selecting a particular level of stimulation on the visual scale.

The pain measuring device 100 may obtain image data representing a change in an external shape of a user according to the stimulation (S730). More specifically, the pain measuring device 100 may obtain information about a facial expression of a user by inputting image data to a trained facial expression analysis model, may obtain information about eyes of a user by inputting image data to a trained eye analysis model, and may obtain information about a gesture of a user by inputting image data to a trained gesture analysis model.

The pain measuring device 100 may obtain biodata representing a biological change of a user according to the stimulation (S740). More specifically, the pain measuring device 100 may obtain at least one of data about a pulse wave of the user, data about an oxygen saturation of the user, and data about an electrocardiogram of the user.

The pain measuring device 100 may obtain information about a level of pain experienced by a user according to stimulation based on data corresponding to a user input, image data, and biodata (S750). More specifically, the pain measuring device 100 may obtain the information about a level of pain experienced by the user according to the stimulation by inputting the data corresponding to the user input, the image data, and the biodata to a trained neural network model.

FIG. 8 is a flowchart illustrating a method of training a neural network model.

With reference to FIG. 8, the pain measuring device 100 according to an embodiment of the present disclosure may receive a user input for recording a level of stimulation according to temperature (S810). The pain measuring device 100 may obtain image data representing a change in an external shape of a user according to the stimulation (S820). The pain measuring device 100 may obtain biodata representing a biological change of a user according to the stimulation (S830). S810 to S830 of FIG. 8 correspond to S720 to S740 of FIG. 7, respectively.

When the user input is received and the image data and the biodata are obtained, the pain measuring device 100 may generate learning data by labeling the image data and the biodata with a level of stimulation corresponding to the user input (S840). More specifically, the pain measuring device 100 may correlate a level of stimulation corresponding to a user input with image data and biodata obtained at the same time point as when the user input is received to label the image data and the biodata with the level of stimulation corresponding to the user input. In this manner, learning data which may be used for supervised learning of the neural network model may be generated.

The pain measuring device 100 may train a neural network model based on the learning data (S850). More specifically, the neural network model may receive not only subjective information such as recordal of level of pain experienced by a user but also objective information such as image data/biodata as an input, and match such information with a quantitative level of pain.

A method of controlling the pain measuring device 100 according to an embodiment may be implemented as a program and provided to the pain measuring device 100. The program including the method of controlling the pain measuring device 100 may be stored and provided in a non-transitory computer-readable medium.

More specifically, in the non-transitory computer-readable medium including the program for executing the method of controlling the pain measuring device 100, the method of controlling the pain measuring device 100 may include controlling a temperature provided from a temperature stimulator, receiving a user input for recording a level of stimulation according to the temperature, obtaining image data representing a change in an external shape of a user according to the stimulation, obtaining biodata representing a biological change of the user according to the stimulation, and obtaining information about a level of pain experienced by the user according to the stimulation based on data corresponding to the user input, the image data, and the biodata.

In addition, in the non-transitory computer-readable medium including the program for executing the method of controlling the pain measuring device 100, the method of controlling the pain measuring device 100 may include receiving a user input for recording a level of stimulation according to temperature, obtaining image data representing a change in an external shape of a user according to the stimulation, obtaining biodata representing a biological change of the user according to the stimulation, generating learning data by labeling the image data and the biodata with a level of the stimulation corresponding to the user input, and training the neural network model based on the learning data.

As such, the method of controlling the pain measuring device 100 and a computer-readable medium including a program for executing the method of controlling the pain measuring device 100 are briefly described only to avoid redundancy, and various embodiments of the pain measuring device 100 may also be applied to the method of controlling to the pain measuring device 100 and the computer-readable medium including a program for executing the method of controlling the pain measuring device 100.

The functions regarding the neural network model described above may be performed by the memory and the processor.

The processor may include a single processor or multiple processors. The single processor or multiple processors may be a general purpose processor, such as a CPU, an application processor (AP), etc., a processor for graphics, such as a GPU, a visual processing unit (VPU), etc., or a processor for artificial intelligence, such as a neural network processing unit (NPU).

Input data may be processed according to a predefined operation instruction or an artificial intelligence model stored in a non-transitory or transitory memory through the control by the single processor or the multiple processors. The predefined operation instruction or artificial intelligence model may be established through learning.

Here, the establishment through learning may mean that a predefined operation instruction or artificial intelligence model of desired characteristics is established by applying a learning algorithm to a plurality of learning data. Such learning may be conducted in a device itself in which an artificial intelligence according to the present disclosure is operated or through a separate server or system.

The artificial intelligence model may include a plurality of neural network layers. Each layer may have multiple weight values and may perform calculation of the layer by using a calculation result of a previous layer and conducting multiple weight calculations. Examples of the neural network include a convolutional neural network (CNN), a deep neural network (DNN), a recurrent neural network (RNN), a restricted Boltzmann machine (RBM), a deep belief network (DBN), a bidirectional recurrent deep neural network (BRDNN), a generative adversarial network (GAN), etc.; however, the neural network of the present disclosure is not limited thereto unless otherwise indicated.

The learning algorithm may be a method to train a certain target device (for example, a robot) by using a plurality of learning data such that the certain target device may make a decision or prediction by itself. Examples of the learning algorithm include supervised learning, unsupervised learning, semisupervised learning, and reinforcement learning; however, the learning algorithm of the present disclosure is not limited thereto unless otherwise indicated.

The machine-readable medium may be provided in a form of a non-transitory medium. The term "non-transitory medium" only means that such medium is tangible device and does not include a signal (for example, an electromagnetic wave), and this term is not intended to show distinction between semi-permanent storage of data and temporary storage of data in a storage medium. For example, the non-transitory medium may include a buffer in which data is temporarily stored.

According to an embodiment, the method according to various embodiments of the present disclosure may be included and provided in a computer program product. The computer program product may be traded as a merchandise between a seller and a buyer. The computer program product may be distributed in a form of a computer-readable medium (e.g., a compact disc read only memory (CD-ROM)) or distributed directly or via online (e.g., download or upload) between two user devices (e.g., smartphones) through an application store (e.g., Play Store™). In the case of online distribution, at least some of the computer program products (e.g., a downloadable application, etc.) may be temporarily stored in a storage medium readable by devices, such as a memory of a manufacturer server, an application store server, or a relay server or temporarily generated.

Each of the aforementioned components (e.g., a module or a program) according to various embodiments of the present disclosure may include a single subcomponent or multiple subcomponents, and some of the aforementioned subcomponents may be omitted or other subcomponents may be further included in various embodiments. Alternatively or additionally, some components (e.g., a module or a program) may be integrated into a single element and perform the same or similar function performed by each component before integration.

Operations performed by a module, a program, or other components according to various embodiments may be performed sequentially, parallely, repetitively, or heuristically, at least some of the operations may be performed in other orders or omitted, or other operations may be added.

The term "portion" or "module" used in the present disclosure may include a unit including a hardware, a software, or a firmware, and may be used inter-compatibly with the terms, such as a logic, a logic block, a part, a circuit, etc. The "portion" or "module" may be an integrated component, a minimum unit performing at least one function, or a part thereof. For example, the module may include an application-specific integrated circuit (ASIC).

The various embodiments of the present disclosure may be implemented as a software including instructions stored in a machine (e.g., computer)-readable storage media. A device may be a device calling a stored instruction from a storage medium and operating according to the called instruction, and may include an electronic device (e.g., the pain measuring device 100) according to the embodiments of the present disclosure.

When an instruction is executed by the processor, the processor may perform a function corresponding to the instruction directly or by controlling other components. The instruction may include a code generated or executed by a compiler or an interpreter.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A pain measuring device comprising:

a plurality of Peltier elements;

a camera;

a sensor;

a memory in which at least one instruction is stored; and a processor configured to execute the at least one instruction, wherein, by executing the at least one instruction, the processor controls a temperature provided from the plurality of Peltier elements, receives a user input for recording a level of stimulation according to the temperature, obtains, from the camera, image data representing a change in an external shape of a user according to the stimulation, obtains, from the sensor, biodata representing a biological change of the user according to the stimulation, and obtains information about a level of pain experienced by the user according to the stimulation by inputting data corresponding to the user input, the image data, and the biodata to a trained neural network model, wherein the plurality of Peltier elements comprises a plurality of first Peltier elements grouped into a first group and a plurality of second Peltier elements grouped into a second group, wherein the plurality of first Peltier elements are arranged to form a different geometric pattern from the plurality of second Peltier elements, and wherein the processor controls the plurality of Peltier elements to provide different temperatures through the first group and the second group, enabling the user to recognize the geometric pattern formed by the plurality of first Peltier elements.

2. The pain measuring device of claim 1, wherein the processor generates learning data by labeling the image data and the biodata with a level of the stimulation corresponding to the user input, and trains the neural network model based on the learning data.

3. The pain measuring device of claim 1, wherein the image data includes at least one of information about a facial expression of the user, information about eyes of the user, and information about a gesture of the user.

4. The pain measuring device of claim 1, wherein the biodata includes at least one of data about a pulse wave of the user, data about an oxygen saturation of the user, and data about an electrocardiogram of the user.

* * * * *